(12) United States Patent
Kanters et al.

(10) Patent No.: US 7,404,881 B2
(45) Date of Patent: Jul. 29, 2008

(54) GAS SENSOR

(75) Inventors: Johannes Kanters, Stuttgart (DE); Johann Riegel, Bietigheim-Bissingen (DE); Lothar Diehl, Gerlingen (DE); Thomas Moser, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 822 days.

(21) Appl. No.: 10/706,889

(22) Filed: Nov. 13, 2003

(65) Prior Publication Data

US 2004/0140213 A1    Jul. 22, 2004

(30) Foreign Application Priority Data

Nov. 13, 2002    (DE)    .................. 102 52 712

(51) Int. Cl.
    *G01N 27/41*    (2006.01)
(52) U.S. Cl. ..................... 204/426; 73/23.32
(58) Field of Classification Search ................. 204/426, 204/424; 205/784.5; 73/23.32
    See application file for complete search history.

(56) References Cited

U.S. PATENT DOCUMENTS

| | | | |
|---|---|---|---|
| 4,505,807 A | | 3/1985 | Yamada |
| 4,755,274 A | | 7/1988 | Mase et al. |
| 4,769,123 A | | 9/1988 | Mase et al. |
| 4,859,307 A | * | 8/1989 | Nishizawa et al. .......... 204/425 |
| 5,250,169 A | | 10/1993 | Logothetis et al. |
| 5,314,604 A | * | 5/1994 | Friese et al. ................. 204/410 |
| 5,507,937 A | | 4/1996 | Renz et al. |
| 5,529,667 A | | 6/1996 | Coffey |
| 5,686,654 A | * | 11/1997 | Friese et al. ................ 73/23.32 |
| 6,375,816 B1 | * | 4/2002 | Jach et al. .................... 204/425 |
| 6,773,565 B2 | * | 8/2004 | Kunimoto et al. ........... 204/425 |
| 2003/0146092 A1 | | 8/2003 | Heimann et al. |

FOREIGN PATENT DOCUMENTS

| | | |
|---|---|---|
| DE | 198 17 012 | 12/1998 |
| EP | 0 310 206 | 1/1993 |
| EP | 0 731 351 | 6/2004 |

\* cited by examiner

*Primary Examiner*—Kaj K Olsen
(74) *Attorney, Agent, or Firm*—Kenyon & Kenyon LLP

(57) ABSTRACT

A gas sensor is described for detecting a physical property of a measuring gas, including detecting the oxygen concentration in the measuring gas. The gas sensor includes a sensor element having a diffusion barrier, which is arranged between a first solid electrolyte layer and a second solid electrolyte layer. The diffusion barrier has a necked-down portion, i.e., a concave profile, between the first and the second solid electrolyte layer. Accordingly, a first area, which the diffusion barrier occupies in a plane which lies between the side of the first solid electrolyte layer (facing the diffusion barrier) and the side of the second solid electrolyte layer (facing the diffusion barrier), is smaller than a second area on which the diffusion barrier covers the first or the second solid electrolyte. In order to manufacture the sensor element, a first layer made of a paste containing a pore-forming material is applied onto a blank foil, and after that, a second layer made of a paste containing a pore-forming material is applied.

18 Claims, 1 Drawing Sheet

GAS SENSOR

FIELD OF THE INVENTION

The present invention relates to a gas sensor and a method for producing a gas sensor.

BACKGROUND INFORMATION

A gas sensor is described, for example, in German Published Patent Application No. 198 17 012. The gas sensor includes a sensor element which is fastened in a housing and is sealed. The sensor element is built up in layers by planar technique, and has a first and a second solid electrolyte layers. Between the two solid electrolyte layers a measuring gas chamber is provided, in which a first and a second annular electrodes are arranged on opposite sides. The measuring gas present outside the sensor elements, whose oxygen concentration is to be determined using the gas sensor, is able to reach the measuring gas chamber via a gas access opening in the first solid electrolyte layer and via a hollow cylinder-shaped diffusion barrier. The diffusion barrier is arranged in the layer plane between the first and the second solid electrolyte layers. The inner and outer lateral surfaces of the diffusion barrier are aligned perpendicular to the layer plane of the sensor element. The gas access opening is produced with the aid of a bore that is carried out right into the diffusion barrier. Consequently, the gas access opening and the diffusion barrier have the same internal diameter. The measuring gas chamber is sealed laterally by a sealing frame. Such planar sensor elements may be produced by printing functional layers onto ceramic blank foils (unsintered solid electrolyte layers) using silk-screen printing. The printed blank foils are laminated together and sintered. The first solid electrolyte layer is formed before sintering by a first blank foil, and the second solid electrolyte layer is formed before sintering by a second blank foil.

In order to produce the structure between the first and the second solid electrolyte layers, for example, the annular first electrolyte is first applied onto the first blank foil, followed by the hollow cylinder-shaped diffusion barrier. Subsequently, over the first electrode, as well as in the opening of the diffusion barrier, a cavity paste containing a pore-forming material is applied, which, after sintering, forms the measuring gas chamber, or rather a section of the gas access opening. Finally, the second electrode is applied over the cavity paste for the measuring gas chamber. The printed first blank foil (print substrate) is laminated together with the non-printed second blank foil.

Because of the silk-screen printing process and on account of the properties of the paste forming the diffusion barrier, the lateral surface of the diffusion barrier, after sintering, is aligned inclined towards the large surface of the sensor element. Consequently, the diffusion barrier has a smaller inside diameter on the side facing the print substrate (first solid electrolyte layer), and a larger outside diameter than on the side facing away from the print substrate. With that, the path the exhaust gas has to travel in the diffusion barrier is greater on the side facing the first solid electrolyte than on the side facing the second solid electrolyte. In oxygen probes that work on the limiting current principle, since the measuring result is a function of the diffusion of the measuring gas through the diffusion barrier, it is desirable for the diffusion barrier to be constructed as symmetrically as possible, so that the path covered by the exhaust gas within the diffusion barrier varies as little as possible.

In diffusion barriers having slanted lateral surfaces, the dependence of the measuring signal on dynamic pressure changes increases. This is undesirable, since, for the engine control, the oxygen concentration in the exhaust gas, and not the partial pressure of the oxygen, is required.

The diffusion barrier may become detached from the second solid electrolyte layer in response to a strong shaking load, since the surface over which the diffusion barrier is connected to the second solid electrolyte is smaller than the surface over which the diffusion barrier is connected to the first solid electrolyte layer (the print substrate).

If the opening in the diffusion barrier is produced with the aid of a bore, so that the opening is aligned perpendicular to the large surface of the sensor element, then the cost of manufacturing the bore becomes expensive, and the inside diameter of the diffusion barrier may not be able to be designed to be greater than the diameter of the gas access opening.

SUMMARY OF THE INVENTION

By contrast, an exemplary gas sensor according to the present invention, as well as an exemplary method according to the present invention for producing the gas sensor, reduce the differences in the diffusion paths through the diffusion barrier in a simple manner from a manufacturing technology point of view. In this regard, the configuration of the diffusion barrier, e.g., the selection of the inside diameter, is not restricted by the manufacturing method.

For this, the diffusion barrier may have two sections. The first section of the diffusion barrier is manufactured in that the paste forming the diffusion barrier after sintering is applied onto the first blank foil (after sintering, first solid electrolyte layer). In a second printing step, the second section of the diffusion barrier is applied on top of the first section of the diffusion barrier. Subsequently, the first blank foil is laminated together with the second blank (the second solid electrolyte layer after sintering) and is sintered. After sintering, the diffusion barrier has a necked-down portion between its two sections.

Hence, the necked-down portion lies in the middle between the first and the second solid electrolyte to thereby minimize the differences in the diffusion paths.

The diffusion barrier may be configured as a hollow cylinder, into interior of which there leads a gas access opening that is inserted into the first solid electrolyte layer. The diffusion barrier may be surrounded by a likewise hollow cylinder-shaped cavity (measuring gas chamber), in which at least one electrode is arranged on the first and/or the second solid electrolyte layer. The measuring gas present outside the exhaust gas may reach the measuring gas chamber via the gas access opening and the diffusion barrier, and consequently reach the electrodes.

According to an exemplary embodiment of the present invention, the gas access opening has a diameter of approximately 0.2 to 0.4 mm. For example, the diameter may be 0.3 mm. The inside diameter of the diffusion barrier, in the vicinity of the necked-down portion, is greater than the diameter of the gas access opening by approximately 0.05 to 0.2 mm. For example, the inside diameter of the diffusion barrier, in the vicinity of the necked-down portion, may be greater than the diameter of the gas access opening by 0.1 mm. As a result of a gas access opening and diffusion barrier which are configured in such a manner, one may minimize the dependence of the measuring signal on dynamic pressure changes, since a dilution effect is achieved for the revving-up setting in.

The first blank foil may be printed in the following sequence: first electrode, first section of the diffusion barrier, measuring gas chamber and inner space of the diffusion barrier (gas access opening) with the aid of a cavity paste, second section of the diffusion barrier, and second electrode (in this connection, the various paste-like print layers are denoted by the elements which form after sintering from the respective print layer).

DETAILED DESCRIPTION

Figure 1:
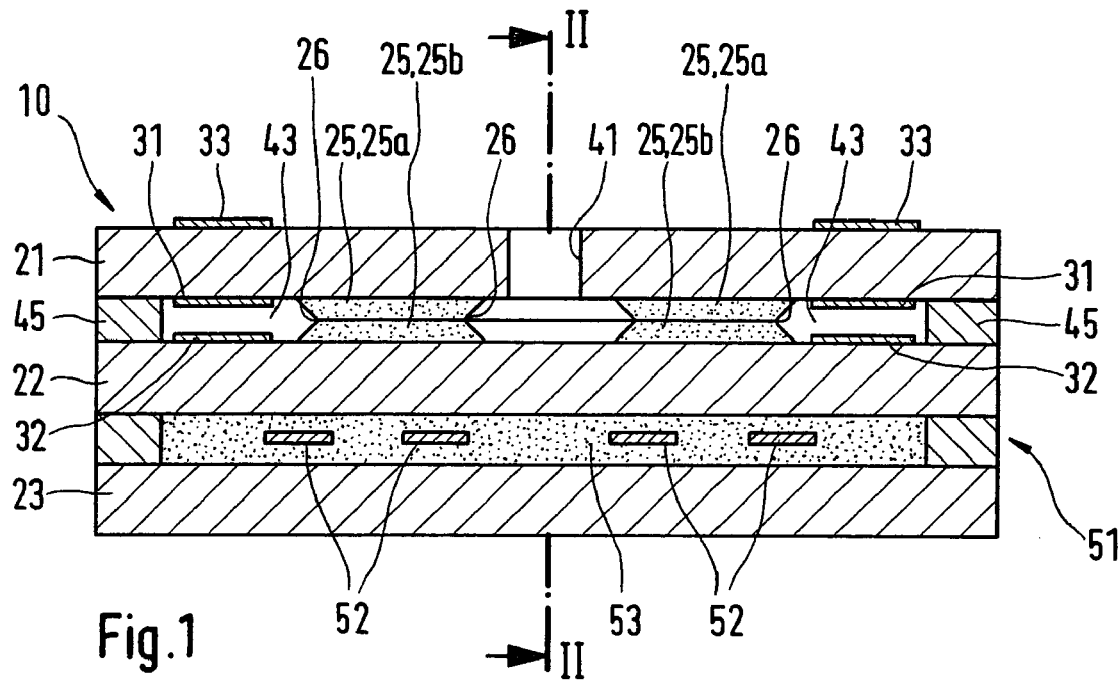
FIG. 1 shows an exemplary embodiment of the present invention in a sectional representation (section perpendicular to the longitudinal axis of the sensor element) taken along line I-I shown in FIG. 2.
Figure 2:
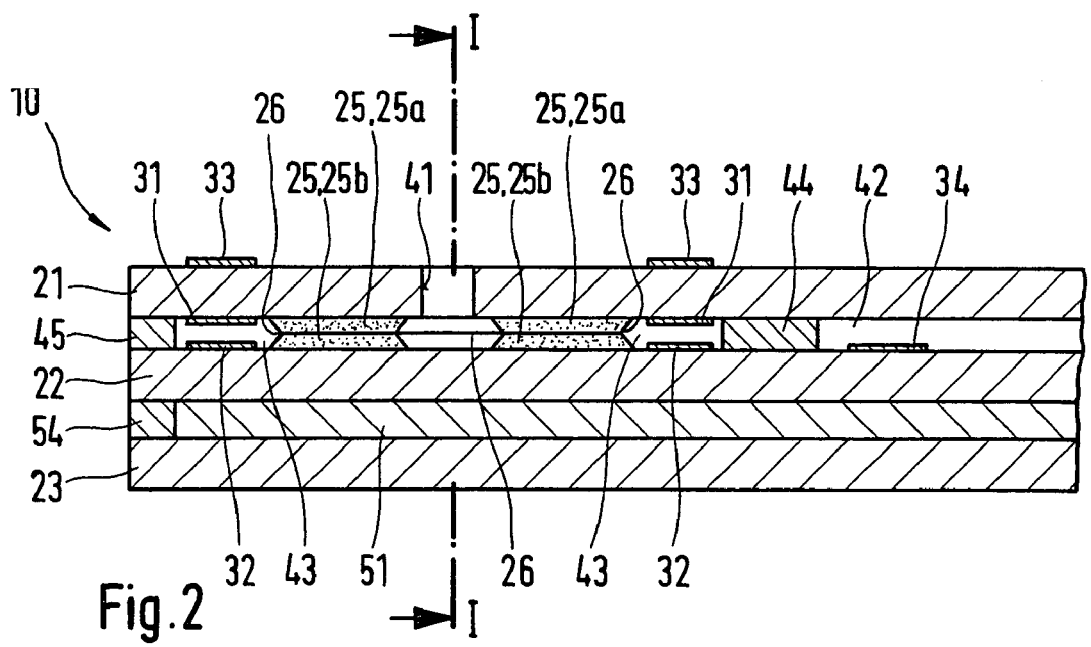
FIG. 2 shows the sensor element in a sectional representation taken along line II-II shown in FIG. 1.

FIG. 1 and FIG. 2 show, as an exemplary embodiment of the present invention, a sensor element 10 having a first solid electrolyte layer 21, a second solid electrolyte layer 22 and a third solid electrolyte layer 23.

Between the second and the third solid electrolyte layer 22, 23, a heating device 51 is provided, which includes a heater 52 and a heater insulation 53. Heater insulation 53 completely surrounds heater 52, and thus insulates heater 52 from surrounding solid electrolyte layers 22, 23.

Between first and second solid electrolyte layer 21, 22, a hollow cylinder-shaped diffusion barrier 25 is arranged, which is surrounded by a measuring gas chamber 43. Measuring gas chamber 43 is likewise formed as a hollow cylinder-shaped cavity. The layer plane between the first and the second solid electrolyte 21, 22, and thus measuring gas chamber 43, is laterally sealed by a sealing frame 45, which reaches right up to the side surfaces of sensor element 10. In the first electrolyte layer 21, whose one large surface forms an outer surface of sensor element 10, a gas access opening 41 is formed, which leads to the center of diffusion barrier 25. Thus, the exhaust gas is able to reach measuring gas chamber 43 via gas access opening 41 and diffusion barrier 25. Between first and second solid electrolyte layer 21, 22, there is also a reference gas chamber 42 which is separated gas-tight from measuring gas chamber 43 by separating element 44. Reference gas chamber 42 contains, as reference atmosphere, a gas having a high oxygen partial pressure, such as atmospheric air.

In measuring gas chamber 43, on first solid electrolyte layer 21, there is an annular first electrode 31, and on second solid electrolyte layer 22, there is an annular second electrode 32. On the outer surface of first solid electrolyte 21 a third electrode 33 is provided, which is covered by a porous protective layer (not shown). In the reference gas chamber 42, on second solid electrolyte layer 22, a fourth electrode 34 is provided.

Second and fourth electrodes 32, 34, together with second solid electrolyte layer 22, form an electrochemical cell, which is operated as a Nernst cell by a wiring configuration arranged outside sensor element 10. First electrode 31 and third electrode 33, as well as first solid electrolyte layer 21, form an additional electrochemical cell, which is operated as a pump cell by the wiring configuration. Consequently, sensor element 10 forms a so-called broadband lambda probe which works according to the limiting current principle. Because of the pump cell, oxygen is pumped into measuring gas chamber 43 or out of measuring gas chamber 43 so that voltage present at the Nernst cell corresponds to an oxygen partial pressure of about lambda=1. The oxygen flowing through diffusion barrier 25 is proportional to the measuring gas present outside sensor element 10. Since all the oxygen flowing into measuring gas chamber 43 is pumped off, i.e., since just as much oxygen is pumped into the measuring gas chamber 43 so that the oxygen almost completely reacts with other gas components, the pump flow of the pump cell is proportional to the partial pressure of the oxygen in the measuring gas. The properties of diffusion barrier 25 therefore have a great influence on the measurement.

The cross-sectional area in the central plane between the first and the second solid electrolyte layer 21, 22 of diffusion barrier 25 is less than the area with which diffusion barrier 25 covers first and/or second solid electrolyte layer 21, 22. Consequently, in the central plane between first and second solid electrolyte layer 21, 22, diffusion barrier 25 has a necked-down portion 26.

In the subsequent description of the exemplary method for manufacturing sensor element 10, the same designations and the same reference numerals are used for the elements of sensor element 10. The solid electrolyte layers are understood to be present before sintering in the form of blank foils. These blank foils may be printed upon, using functional layers present in paste form, employing silk-screen technology. The paste-like functional layers differ in their composition. Thus, for example, electrodes 31, 32, 33, 34 or heater 52 are printed onto the blank foils in the form of a platinum-containing cermet paste. For insulating layers (heater insulation 53), pastes containing aluminum oxide are used. In order to manufacture a porous layer (diffusion barrier 25) or a cavity (measuring gas chamber 43), pastes are used which contain a pore-forming material which volatilize during sintering. The different compositions of the paste-like functional layers are understood to be conventional.

In order to manufacture sensor element 10, the following layers may be applied onto first solid electrolyte layer 21 in the sequence given: first electrode 31; first section 25a of diffusion barrier 25; onto first electrode 31 a cavity paste for measuring gas chamber 43, as well as, in the same printing step, the cavity paste in the vicinity of gas access opening 41; onto first section 25a of diffusion barrier 25 second section 25b of diffusion barrier 25; and onto the cavity paste for measuring gas chamber 43 second electrode 32. Furthermore, in additional printing steps, the following elements are printed onto first solid electrolyte layer 21: sealing frame 45, separating element 44, and fourth electrode 34 as well as the cavity paste for reference gas chamber 42.

Onto third solid electrolyte layer 23 is printed a first section of heater insulation 53, heater 52 onto that, and onto the heater 52, in turn, a second section of heater insulation 53. The two sections of heater insulation 53 are not explicitly shown as discrete sections in the figures. First solid electrolyte layer 21 is printed upon on both sides. On the side of first solid electrolyte layer 21 forming the outer surface of sensor element 10, third electrode 33 as well as the protective layer (not shown) covering the third electrode are printed.

The solid electrolyte layers printed upon are laminated together. After that, gas access opening 41 is formed in first solid electrolyte layer 21. Alternatively, gas access opening 41 may also be formed in the first solid electrolyte layer even before laminating together, for example, by stamping. The laminate composite is subsequently sintered. On account of the properties of the pastes for diffusion barrier 25, a necked-down portion develops on the inner and outer lateral surface of hollow cylinder diffusion barrier 25, between the two sections 25a, 25b.

What is claimed is:

1. A gas sensor for detecting a physical property of a measuring gas, comprising:
   a first solid electrolyte layer;
   a second solid electrolyte layer; and
   a diffusion barrier arranged between the first solid electrolyte layer and the second solid electrolyte layer, wherein the diffusion baffler has a portion with a concave cross-sectional profile between the first and the second solid electrolyte layers in a cross-sectional plane transverse to the first and second solid electrolyte layers.

2. The gas sensor of claim 1, wherein the sensor is configured to detect an oxygen concentration in the measuring gas.

3. The gas sensor of claim 1, wherein the portion with a concave cross-sectional profile lies in a layer plane in a central region between the first and the second solid electrolyte layers.

4. The gas sensor of claim 1, wherein the diffusion baffler is hollow cylinder-shaped, and wherein the first solid electrolyte layer includes a gas access opening to connect the diffusion barrier to the measuring gas outside the sensor element.

5. The gas sensor of claim 4, wherein the portion with a concave cross-sectional profile is arranged on at least one of an outer and an inner lateral surface of the hollow cylinder-shaped diffusion barrier.

6. The gas sensor of claim 4, wherein the gas access opening has a diameter of 0.2 to 0.4 mm, and wherein an inside diameter of the diffusion barrier, in a region of the portion with a concave cross-sectional profile, is greater than the diameter of the gas access opening by 0.05 to 0.2 mm.

7. The gas sensor of claim 6, wherein the gas access opening has a diameter of 0.3 mm.

8. The gas sensor of claim 6, wherein an inside diameter of the diffusion baffler, in a region of the portion with a concave cross-sectional profile, is greater than the diameter of the gas access opening by 0.1 mm.

9. The gas sensor of claim 4, further comprising:
   a hollow cylinder-shaped measuring gas chamber bordered by the first and second solid electrolyte layers and configured as a cavity to surround the diffusion barrier.

10. The gas sensor of claim 9, wherein a volume of the measuring gas chamber is larger than a volume of the diffusion barrier by a factor of 3 to 7.

11. The gas sensor of claim 9, wherein a volume of the measuring gas chamber is larger than a volume of the diffusion barrier by a factor of 4.

12. The gas sensor of claim 4, further comprising:
   a first electrode that is reachable by the measuring gas present outside the sensor element, through the gas access opening and the diffusion barrier.

13. The gas sensor of claim 12, wherein the first electrode in the measuring gas chamber is arranged on the first solid electrolyte layer.

14. The gas sensor of claim 12, further comprising:
   a second electrode arranged on the second solid electrolyte layer in the measuring gas chamber on a side lying opposite to the first electrode.

15. The gas sensor of claim 1, further comprising:
   a heating device having a heater and a heater insulation, the heater insulation electrically insulating the heater from surrounding solid electrolyte layers.

16. A gas sensor for detecting a physical property of a measuring gas, comprising:
   a first solid electrolyte layer;
   a second solid electrolyte layer; and
   a diffusion baffler arranged on parallel opposed surfaces between the first solid electrolyte layer and the second solid electrolyte layer, wherein the diffusion baffler includes a first area and a second area, the first area lying in a first plane positioned between the first and second solid electrolyte layers, the second area lying in a second plane between the first and second solid electrolyte layers and covering one of the first and the second solid electrolyte layers, and wherein the first area is smaller than the second area;
   wherein a smallest cross-sectional area of the diffusion baffler lies in a central plane extending parallel to, and between, the first and the second solid electrolyte layers.

17. The gas sensor of claim 16, wherein the sensor is configured to detect an oxygen concentration in the measuring gas.

18. The gas sensor of claim 17, wherein the first area lies in a central region between the first and the second solid electrolyte layers.

* * * * *